United States Patent [19]

Degen et al.

[11] 4,291,123
[45] Sep. 22, 1981

[54] PRODUCTION OF FRUCTOSE AND FRUCTOSE-BASE SYRUPS AND MEANS FOR CARRYING OUT SUCH PRODUCTION

[75] Inventors: Ludwig Degen; Paolo Branduzzi; Roberto Olivieri; Nadia Cimini, all of Rome, Italy

[73] Assignee: Snamprogetti, S.p.A., Milan, Italy

[21] Appl. No.: 913,536

[22] Filed: Jun. 8, 1978

[30] Foreign Application Priority Data

Jul. 5, 1977 [IT]  Italy ............................... 25380 A/77

[51] Int. Cl.³ ............................................ C12P 19/24
[52] U.S. Cl. ..................................... 435/94; 435/234; 435/886
[58] Field of Search .................................. 435/94, 234

[56] References Cited

U.S. PATENT DOCUMENTS

| | | | |
|---|---|---|---|
| 3,616,221 | 10/1971 | Takasaki et al. | 435/234 |
| 3,625,828 | 12/1971 | Brownewell | 435/234 |
| 3,957,587 | 5/1976 | Armbruster et al. | 435/234 |

*Primary Examiner*—Lionel M. Shapiro
*Attorney, Agent, or Firm*—Morgan, Finnegan, Pine, Foley & Lee

[57] ABSTRACT

A method is disclosed for the production of fructose and syrups containing fructose and glucose, comprising the step of contacting a solution of glucose with a micro-organism of the genus Streptomyces sp. and more particularly of the strains NRRL 11.120 and NRRL 11.121, as designated by the Northern Regional Research Center, U.S. Department of Agriculture, Peoria, Ill.

1 Claim, No Drawings

PRODUCTION OF FRUCTOSE AND FRUCTOSE-BASE SYRUPS AND MEANS FOR CARRYING OUT SUCH PRODUCTION

This invention relates to a method for the production of fructose and syrups containing fructose and glucose by using an isomerizing enzyme obtained from microorganism of the Streptomyces genus, and to the means which are required for carrying said method into effect.

For the enzymic isomerization of glucose into fructose, glucose isomerase (D-xylose-ketol-isomerase, 5.3.1.5.) is added to a solution of glucose, such as corn syrup, and the reaction conditions are controlled in such a way that a fraction of glucose is converted into fructose, the amount of glucose which is converted into fructose being a function of an equilibrium constant which, at 60° C., is 1.

A number of disclosures describe enzymic processes for the conversion of glucose into syrups which contain glucose and fructose by exploiting enzymes extracted from a number of species of microorganisms of the genera Pseudomonas, Lactobacillus, Escherichia, Aerobacter, Bacillus and others.

It has now been found, and this is a first feature of the present invention, that also Streptomyces sp. strains, not described heretofore, are capable of producing an isomerizing enzyme active on glucose, when grown on an appropriate culturing medium.

These strains, isolated from wood lots in the botanical garden of Pavia, Italy, are marked with the numbers Cl 71/A and Cl 77/22 and are deposited in the Northern Regional Research Center, U.S. Department of Agriculture, Peoria, Ill. under the numbers NRRL 11.120 and NRRL 11.121.

They have the characteristics which are reported below:

|   |   | Cl 71/A | Cl 77/22 |
|---|---|---|---|
| A. | Color of the mature and sporified mycelium | grey (Gy) | grey (Gy) |
| B. | Morphology of the sporangia | reactus flexibilis (RF) | reactus flexibilis (RF) |
| C. | Dark brown melanoid pigments | present (C+) | present (C+) |
| D. | Surface of the spores | smooth (SM) | smooth (SM) |
| E. | Assimilation of C sources: | | |
|   | D-glucose | + | + |
|   | D-xylose | + | + |
|   | D-arabinose | + | + |
|   | D-rhamnose | − | − |
|   | D-fructose | + | (+) |
|   | D-galactose | + | + |
|   | Raffinose | − | + |
|   | D-mannitol | − | − |
|   | i-inositol | + | (+) |
|   | Salicin | + | + |
|   | Sucrose | − | − |
| F. | Formation of compounds having an antibiotic activity | None | None |
| G. | Color of the vegetative mycelium | Cream to light brown | Cream to light brown |
| H. | Sensitivity against streptomycin | sensitive | sensitive |

The tests, with the exclusion of E. were carried out on Fe-Co Asparagine agar. For the test of utilization of the several C-sources, E., the basal medium by Pridham and Gottlieb (1948) was used.

According to the disclosure in the Bergey's Manual of Determinative Bacteriology, 8th Edition (1974), the Streptomyces sp. strains Cl 71/A and Cl 77/22 belong to the grey series and differ by two or more characteristics from the biochemical standpoint, from the 25 species inserted in the series concerned.

The cultures of micro-organisms which lie within the scope of this invention can be grown under aerobic conditions with any conventional method, such as surface cultures or, preferably, in a submerged culture, using stirred fermentors. A culturing medium, which can be either solid or liquid, contains an assimilable C-source, a nitrogen source, as well as mineral salts and trace elements.

As carbon sources, there can be used malt extract, glucose, maltose, sucrose and other sugars, glycerol, corn steep liquor, aminoacids, peptides and others. As nitrogen sources, organic or inorganic nitrogen compounds can be used, such as yeast extract, peptones, tryptones, meat extract, aminoacids, casein hydrolysates, soybean flour, salts of $NO_3^-$ and of $NH_4^+$. For a satisfactory growth, other trace elements are required, such as magnesium, cobalt, phosphorus, sulphur and growth-simulating factors.

An outstanding advantage of the Streptomyces strains which are the subject matter of this invention, is the fact that they are in a position to hydrolyze xylans.

Xylose, commonly used as an inductor of the enzymic activity, is at a premium and the possibility of using, in its stead, xylans which are widespread in natural occurrence (wheat straw: 15% to 20%, bagasse 30%, Coniferae wood from 7% to 12%, Broadleaf Evergreens: from 20% to 25%: oily seed hulls: 25% to 30%), is actually an asset. Xylose can be obtained also by acidic hydrolysis of xylans. Regrettably enough, undesirable or toxic products are formed during the acidic hydrolysis, such as furfural, hydroxymethylfurfural and levulinic acid.

An appropriate culturing medium has, by way of example, the following composition:

| Yeast extract | 5 to 20 grams/liter (g/l) |
|---|---|
| glucose | 10 g/l |
| traces of $KH_2PO_4$, $MgSO_4$ | |
| $NH_4Cl$, or $NaNO_3$ | 1 g/l |

The solution is brought to a pH 7 with soda or phosphate buffer. The pH range which is appropriate for the culture of from 5 to 9, the interval from 6.8 to 7.3 being preferred, and the temperature is between 20° C. and 40° C., the 29° C.–31° C. interval being preferred.

It has proven to be an advantage to split the growing phase from the induction phase. In the practice, the inductors, xylose or xylans, are added after the growth phase of the micro-organisms.

If, in the culturing medium glucose has been used as the carbon source, it is appropriate to collect the biomass by centrifuging it to separate it from the culturing medium and to transfer such mass in the induction medium which contains 0.5% to 2% of xylose together with $Co^{++}$ and $Mg^{++}$ ions.

The extraction of the glucose isomerase from the mycelium takes place with the methods which are conventional in enzymology.

To this end, the cells are disintegrated with specially provided machines such as French Pressure Cell, Manton Gaulin Homogenizer, rotary disintegrators and others, or with the aid of ultrasonic appliances. The enzyme can be equally well extracted from acetonic powders or from freeze-dried extracts.

Glucose isomerase, as obtained from microbial strains, these being a subject matter of this invention, is characterized by a satisfactory stability to heat.

The isomerization of glucose can take place by any conventional method. The glucose solution can directly be added to a culture of micro-organisms, that is to fresh mycelium, or to mycelium which has been freeze-dried and stored, as well as to acetonic powder or to freeze-dried mycelium. In these cases it is necessary that the isomerization be stabilized by treating the mycelium for 30 mins. at 75° C. with a pH of 7.5.

It is also possible to use preparations which contain isomerase in the form of extracts of their concentrates, preparations or raw or purified isomerase and which have been obtained from the mycelia of the above enumerated micro-organisms.

Lastly, a further technical and economical improvement can be achieved by immobilizing the enzyme by combinations of macromolecular compounds by forming chemical bonds with the matrix, or bonds of a ionic type, or by physical immobilization.

The following examples make other procedural details conspicuous, related to the present invention but without limiting same.

EXAMPLE 1

A culturing broth is prepared, which has the following composition:

| Yeast extract | 10 g/l |
|---|---|
| Enzymic casein hydrolysate | 10 g/l |
| NA$_2$HPO$_4$ . 12H$_2$O | 6 g/l |
| KH$_2$PO$_4$ | 3 g/l |
| NH$_4$Cl | 1 g/l |
| MgSO$_4$ . 7H$_2$O | 0.2 g/l |
| glycerol | 10 g/l | the ingredients listed above being dissolved in deionized water and brought to a pH of 7.0 with soda.

The so prepared culturing medium is distributed among 500-ml broad necked flasks, placing 100 mls of broth per flask. Sterilization is carried out at 116° C. during 30 mins.

The broths are inoculated with a sterile deionized water suspension of spores of the strain Cl 71/A of Streptomyces, grown for 4–5 days at 30° C. on Asparagin Fe-Co slants. The slants are composed as follows:

| L-asparagin | 10 g/l | |
|---|---|---|
| Beef extract | 2 g/l | |
| KH$_2$PO$_4$ | 0.5 g/l | |
| CoCl$_2$ . 6H$_2$O | 1 milligram (mg) per liter (l) | from a freshly prepared solution. |
| FeSO$_4$ . 7H$_2$O | 1 mg/l | |
| Xylose | 10 g/l | |
| Agar | 20 g/l | | these components being dissolved in deionized water and the resultant solution being adjusted to a pH of 7.0 with soda. Sterilization is carried out at 116° C. for 30 mins. Incubation is carried out with orbital stirring (220 rpm) at 30° C. 24 hours as from inoculation, there are added to each flask 1 g of xylose and 0.024 g of CoCl$_2$.6H$_2$O. After 24 additional hours of incubation, the cells are collected by centrifuging and washed with an Na$_2$SO$_3$ 0.1 M buffer, pH 7.0, containing Co$^{++}$ 10$^{-4}$ M and Mg$^{++}$ 5.10$^{-3}$ M.

100 mls of such a broth culture gave 4.9 g of moist cells.

These cells were reslurried in 49 mls of the pH 7.0, 0.1 M Na$_2$SO$_3$ buffer mentioned above (1 g of moist cells in 10 mls buffer) and the cellule slurries were passed through a French Pressure Cell press until breaking the cells. In the raw extract thus obtained the enzymic activity was determined: 1 g of moist cells contained 290 enzyme units.

A portion of moist cells had been placed in a vacuum oven so as to determine the dry weight and, from 1.76 g of moist cells, 0.340 g of dried cells has been obtained. The enzymic activity was determined in the following manner: To a reaction mixture containing: 4.5 mls of a solution of substrate (D-glucose 3.67 M, Mg$^{++}$ 5.10$^{-3}$ M, Co$^{++}$ 10$^{-4}$ M, Na$_2$SO$_3$ 0.1 M in deionized, pH 7.0 water), 0.5 ml of raw extract were added. The incubation took place for 2 hours on a water bath at 60° C. The reaction was discontinued by cooling the mixture to 0° C. The optical rotations of the sample ($\alpha_{2\,hrs}$) and of the sample ($\alpha_o$) were measured at room temperature in a Perkin-Elmer 141 polarimeter, sodium line (549 nm), optical path of the cuvette = 0.1 dm.

Should we define as SNAMPROGETTI-Unit that portion of the enzyme which produces 1 milligram (1 mg) of fructose an hour under the test conditions specified above, the enzyme units per g of moist cells are can be calculated by the following relationship: SNAMPROGETTI Units per gram of moist cells =

$$\frac{(\alpha_o - \alpha_{2h}) \cdot (\text{mg of test glucose}) \cdot 10}{(\alpha_{gluc.}) - (\alpha_{fruct.}) \cdot 0.1 \cdot C \cdot 0.5 \cdot 2}$$

wherein:

($\alpha_{gluc.}$) = +54°.16

($\alpha_{fruct.}$) = −98°.35

C = g/ml 0.1 = optical bath, in decimeters (1 dm = 0.1 meter).

EXAMPLE 2

Broth cultures of the Cl 77/22 Streptomyces strain, prepared as explained in Example 1, are incubated with orbital stirring at 30° C.

24 hours as from the inoculation, there are added to each flask 1 g of xylose and 0.024 g of CoCl$_2$.6H$_2$O. After 24 additional hours of incubation at 30° C., the cells are collected by centrifuging and washed with Na$_2$SO$_3$ 0.1 M pH 7 buffer, containing Co$^{++}$ 10$^{-4}$ M and Mg$^{++}$ 5.10$^{-3}$ M.

5.2 grams of moist cells were obtained from 100 mls of this broth culture.

These cells were reslurried in 52 mls of the Na$_2$SO$_3$ 0.1 M pH 7.0 buffer aforementioned (1 g of moist cells in 10 mls of buffer) and the cell slurried passed to a French Pressure Cell press until the cells were broken. In the extract thus obtained the enzymic activity was determined and 1 g of moist cells was found to contain 300 enzymic units.

A portion of moist cells had been placed in a vacuum oven to determine the weight: from 1.80 g of moist cells, 0.312 g of dried cells have been obtained.

EXAMPLE 3

Broth cultures of the Cl 71/A Streptomyces strain, which had been prepared according to Example 1 and inoculated in a growth medium having the same composition of that of Example 1, with the only exception that glycerol has been replaced by xylans, as C-source, are put to incubation with stirring at 30° C. After 24 hrs as from the inoculation, there is added to each flask 0.024 g of $CoCl_2.6H_2O$. After 24 additional hours of incubation, the cells are collected by centrifuging and washed with an $Na_2SO_3$ 0.1 M pH 7.0 buffer containing $Co^{++} 10^{-4}$ M and $Mg^{++} 5.10^{-3}$ M. 100 mls of such a broth culture gave 3.3 g of moist cells. These cells were reslurried in 33 mls of the $Na_2SO_3$ 0.1 M pH 7.0 buffer aforesaid (1 g of cells in 10 mls buffer) and the cell slurries were passed to the French Pressure Cell press until breaking such cells. The enzymic activity was determined in the extract so prepared and 1 g of cells gave 190 enzymic units.

EXAMPLE 4

Broth cultures of the Cl 77/22 Streptomyces strain prepared according to Example 3, were put to incubate with stirring at 30° C. After 24 hours as from the inoculation there is added to each flask 0.024 g of $CoCl_2.6H_2O$. After 24 additional hours of incubation at 30° C., the cells are collected by centrifuging them and washed with an $Na_2SO_3$ 0.1 M pH 7.0 buffer containing $Co^{++} 10^{-4}$ M and $Mg^{++} 5.10^{-3}$ M. 100 mls of this broth culture gave 3.2 g of moist cells. These cells were reslurried in 32 mls of the $Na_2SO_3$ 0.1 M pH 7.0 buffer aforementioned (1 g of moist cells in 10 mls buffer) and the cell slurries were passed through the French Pressure Cell press until the cells had been broken.

The enzymic activity was determined in the extract thus obtained and 1 g of moist cells contained 200 enzymic units.

EXAMPLE 5

Broth cultures of the Streptomyces Cl 71/A strain were prepared and the cells induced as in Example 1.

On completion of the induction stage, the cells are collected by centrifugation and washed with an $Na_2SO_3$ 0.1 M pH 7 buffer containing $Co^{++} 10^{-4}$ M and $Mg^{++} 5.10^{-3}$ M. From 400 mls of this broth culture 18.3 g of moist cells were obtained.

6.2 g of moist cells were reslurried in 25 mls of an $Na_2SO_3$ 0.1 M pH 7.0 buffer and added, with stirring at $-10°$ C., to 120 mls of acetone. After 15 mins. of treatment, the cells were collected on a paper filter, washed with acetone, collected and dried in a vacuum at room temperature. From 6.2 g of moist cells 1.1 g of dried cells were thus obtained. On the acetonic powder the enzymic activity was determined and 1 g of cells treated with acetone contained 2,370 units of enzyme.

EXAMPLE 6

Broth cultures of the Cl 77/22 Streptomyces strain were prepared and the cells were induced as in Example 1. On completion of the induction step, the cells were collected by centrifugation and washed with an $Na_2SO_3$ 0.1 M pH 7.0 buffer containing $Co^{++} 10^{-4}$ M and $Mg^{++} 5.10^{-3}$ M. From 400 mls of such broth culture there were obtained 28.2 g of moist cells. 9.2 g of moist cells were reslurried in 25 mls of the $Na_2SO_3$ 0.1 M pH 7.0 buffer and added, with stirring and at the temperature of $-10°$ C., to 120 mls acetone. After a 15-minute treatment, the cells were collected on a filter paper, washed with acetone, collected and dried in a vacuum at room temperature. From 9.2 g of moist cells, 1 g of dried cells was thus obtained.

On the acetonic powder the enzymic activity was determined and it was found that 1 g of acetone-treated cells contained 2,100 enzymic units.

EXAMPLE 7

Cells of the Streptomyces Cl 77/A strain are prepared as detailed in Example 1 and treated with acetone as detailed in Example 5.

The cells treated with acetone are used for determining the percentage of isomerization of glucose as a function of time in the reaction mixture.

The testing conditions were as follows:
(a) Cells treated with acetone: 10 g
(b) Volume of substrate: 1 liter
(c) Reaction temperature: 60° C.

The substrate has the following composition: glucose 60% (wt/vol), $Mg^{++}$ 5 mM, $Co^{++}$ 0.1 mM, $Na_2SO_3$ 100 mM, pH 7.0.

The isomerization percentages were as follows:

| Time, hrs. | Conversion, % |
|---|---|
| 3 | 12 |
| 6 | 20 |
| 9 | 27.2 |
| 12 | 32.6 |
| 15 | 37.1 |
| 18 | 40.5 |
| 23 | 44.5 |

We claim:
1. A method for the production of fructose and syrups containing fructose and glucose, said method comprising contacting a solution of glucose with a Streptomyces sp. NRRL 11,120 or NRRL 11,121 or with enzyme originated thereby.

* * * * *